United States Patent [19]

Chen

[11] Patent Number: 5,405,327

[45] Date of Patent: Apr. 11, 1995

[54] SIMPLIFIED SAFETY SYRINGE WITH RETRACTABLE SELF-BIASED NEEDLE AND MINIMIZED PLUNGER

[76] Inventor: Long-Hsiung Chen, C/O Hung Hsing Patent Service Center P.O. Box 55-1670, Taipei, Taiwan, Prov. of China

[21] Appl. No.: 282,640

[22] Filed: Jul. 29, 1994

[51] Int. Cl.⁶ .............................................. A61M 5/00
[52] U.S. Cl. ................................... 604/110; 604/195; 128/919
[58] Field of Search ............... 604/110, 187, 192, 195, 604/198, 263; 128/919

[56] References Cited

U.S. PATENT DOCUMENTS 5,125,898  6/1992  Kaufhold, Jr. et al. ............ 604/110
5,171,300  12/1992  Blake, III et al. .................. 604/110
5,211,628  5/1993  Marshall ......................... 604/195 X Primary Examiner—John D. Yasko

[57] ABSTRACT

A safety syringe with a minimized thin-disk plunger for saving cost includes: a hollow needle normally held in a front portion of a syringe, a coupling member of arrowhead shape integrally formed with the thin-disk plunger, an annular ring embedded on the plunger to allow the plunger to be slidably held in the syringe for injection use, the coupling member formed on the plunger engageable with a biasing socket recessed in a rear needle portion of the hollow needle and with the biasing socket generally formed as a conical shape having a longitudinal conical axis inclined from a needle axis of the needle, whereby upon retraction of the plunger and the coupled needle into the syringe, the needle will be inclined to prevent a further outward protruding of the retracted needle.

1 Claim, 3 Drawing Sheets

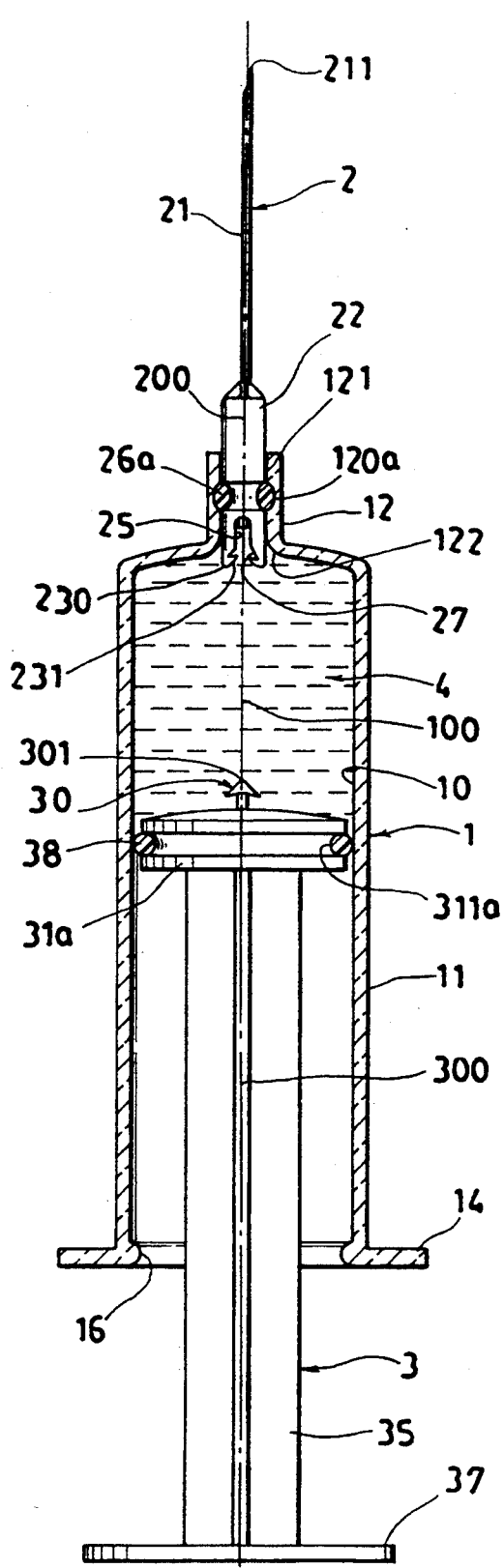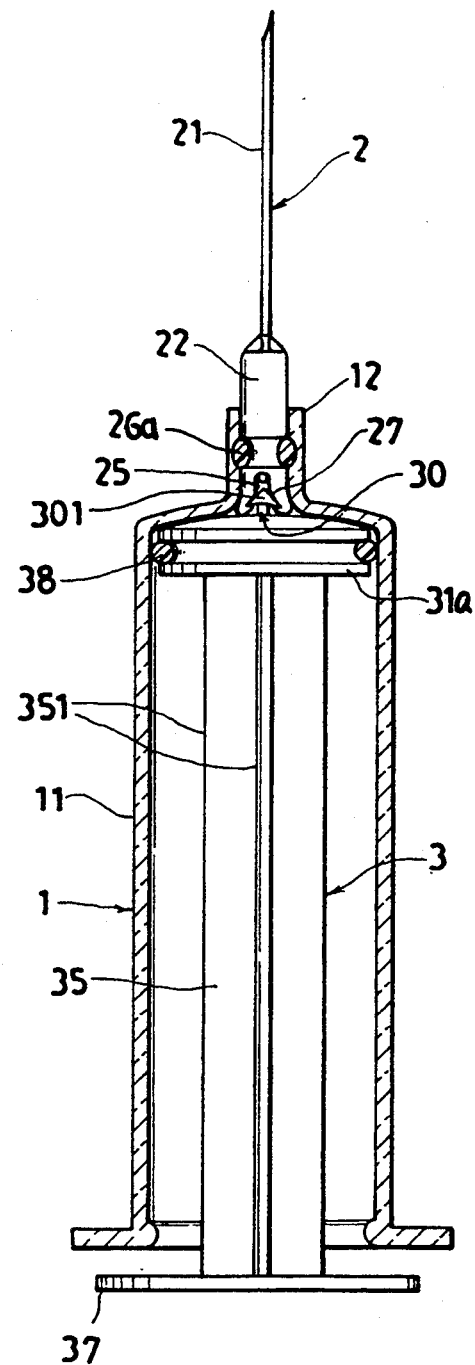
FIG.2
FIG.3

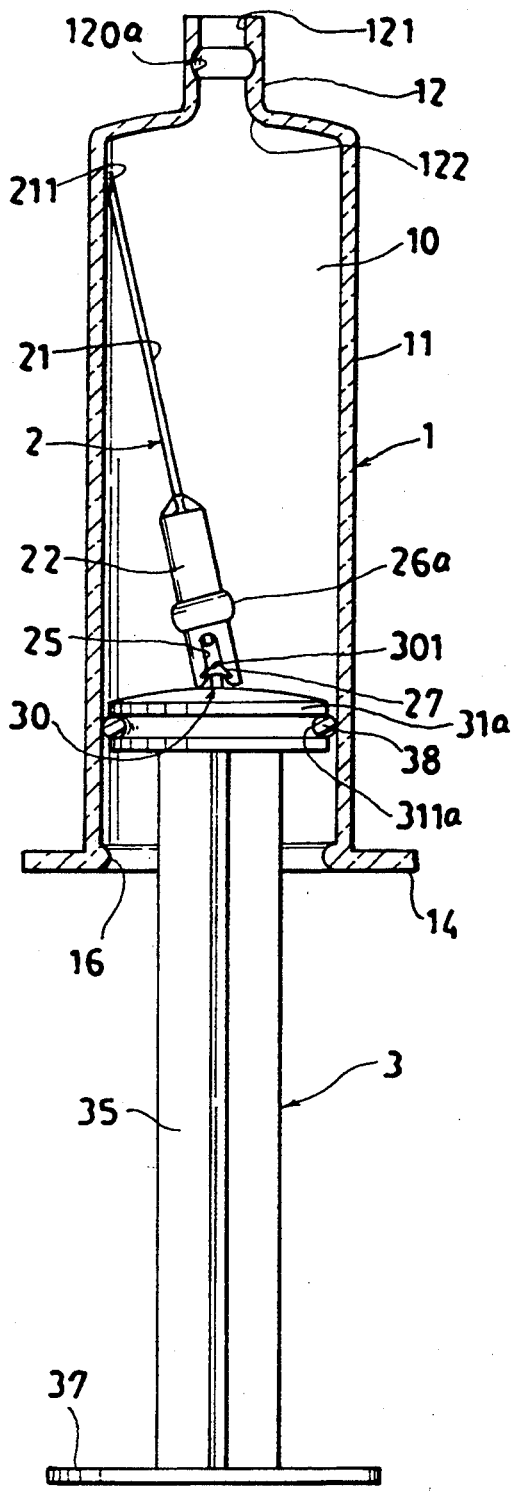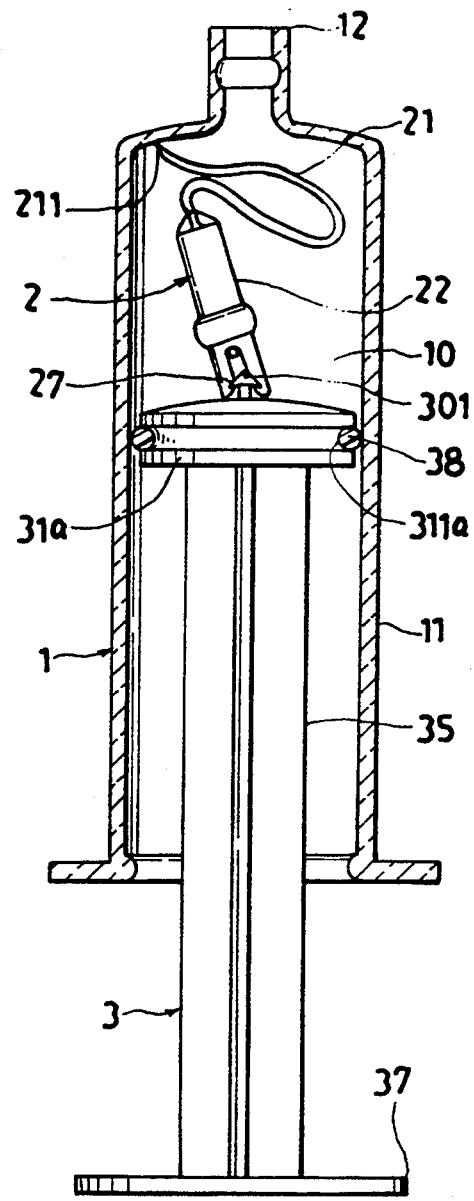
FIG.4
FIG.5

SIMPLIFIED SAFETY SYRINGE WITH RETRACTABLE SELF-BIASED NEEDLE AND MINIMIZED PLUNGER

BACKGROUND OF THE INVENTION

U.S. Pat. No. 5,328,475 entitled "Simplified Safety Syringe with Retractable Self-biased Needle" issued to the same inventor of this application disclosed a safety syringe including: a hollow needle normally held in a front portion of a syringe, a plunger generally cylindrical shaped and slidably held in the syringe for injection use, a coupling member retained in the plunger and engageable with a biasing socket recessed in a rear needle portion of the hollow needle and with the biasing socket generally formed as a conical shape having a longitudinal conical axis inclined from a needle axis of the needle when normally fixed in the syringe with the needle axis aligned with a syringe axis longitudinally formed in a center line of the syringe, whereby upon retraction of the plunger and the needle coupled to the plunger, with the biasing socket of the needle forcibly coupled with the coupling member, into a bore portion in the syringe, the needle will be automatically inclined as the biasing socket of the needle is restored by the coupling member retained in the plunger to prevent an outward protruding of the retracted needle from the syringe for preventing its pricking to the others.

However, the plunger (31) secured on the coupling member (30) will require a big volume in order to efficiently surround the arrowhead portion (301) on the coupling member (30) and to engage the conical base portion (303) of the coupling member (30). Since the safety syringe is always made as disposable and will be disposed once being used for hygienic reason, such a big plunger, which is always made of resilient rubber materials, will waste money and will also increase a burden for waste disposal and treatment on a viewpoint of environmental protection.

SUMMARY OF THE INVENTION

The object of the present invention is to provide a safety syringe having a minimized thin-disk plunger for saving cost and including: a hollow needle normally held in a front portion of a syringe, a coupling member of arrowhead shape integrally formed with the thin-disk plunger, an annular ring embedded on the plunger to allow the plunger to be slidably held in the syringe for injection use, the coupling member formed on the plunger engageable with a biasing socket recessed in a rear needle portion of the hollow needle and with the biasing socket generally formed as a conical shape having a longitudinal conical axis inclined from a needle axis of the needle whereby upon retraction of the plunger and the coupled needle into the syringe, the needle will be inclined to prevent a further outward protruding of the retracted needle.

BRIEF DESCRIPTION OF THE DRAWINGS

FIG. 2 is an illustration showing the present invention when served for injection use.

FIG. 3 shows coupling of the plunger with the needle when finishing a medical injection.

FIG. 4 shows retraction of needle into the syringe of the present invention.

FIG. 5 shows a bent needle in the syringe in accordance with the present invention.

DETAILED DESCRIPTION

Figure 1:
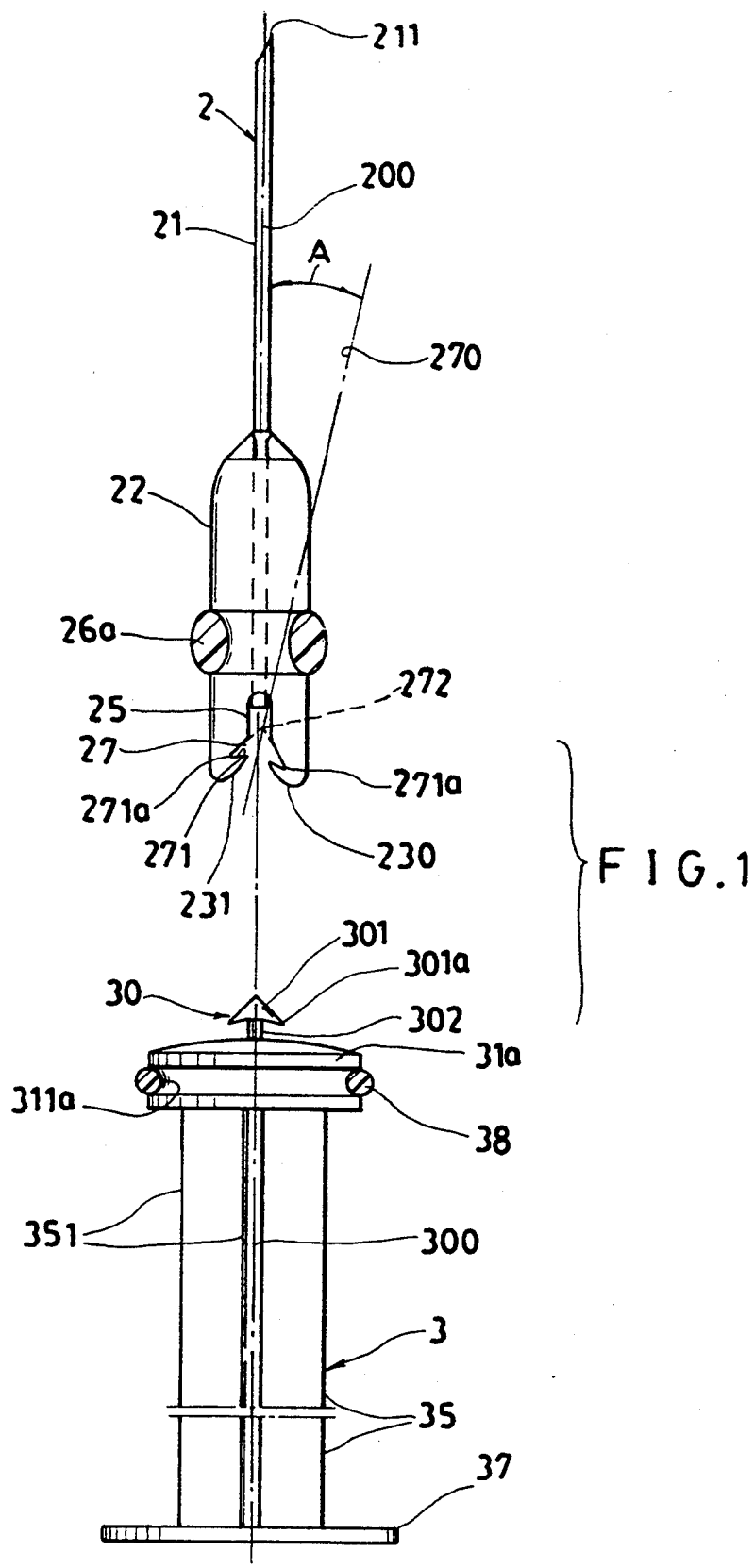
FIG. 1 is an illustration showing the plunger and the needle in accordance with the present invention.

As shown in the drawing figures, the present invention comprises: a syringe means 1, a needle device 2, and a plunger means 3.

The syringe means 1 includes: a syringe cylinder 11 having a hollow bore portion 10 defined in the syringe cylinder 11 for filling liquid medicine 4 in the cylinder 11 and a syringe axis 100 longitudinally defined in a central portion of the syringe cylinder 11, a sleeve portion 12 formed on a front portion of the syringe cylinder 11 contracted forwardly from the cylinder having a central opening 121 formed through the sleeve portion 12, and a diverging port 122 formed in a rear portion of the sleeve portion 12 adjacent to the syringe cylinder 11, an arcuate recess 120a circumferentially recessed in a front portion of the sleeve portion 12, a syringe handle 14 formed on a rear end portion of the cylinder 11, and an annular extension 16 annularly formed on a rear portion of the cylinder 11.

The needle device 2 includes: a needle portion 21 having a needle tip 211 formed at a front end of the needle portion 21, a shank portion 22 connected with the needle portion 21 having an arcuate packing ring 26a circumferentially disposed around the shank portion 22 to be engageably held in the ring groove 120a in the sleeve portion 12, a bifurcated slot 25 longitudinally formed in a rear portion of the shank portion 22 and recessed forwardly from a rear needle end portion 230, a biasing socket 27 generally conical shaped formed in a rear portion of the shank portion 22 and communicating with a guiding port 231 recessed forwardly from the rear needle end portion 230, and a needle axis 200 longitudinally defined at a central portion of the needle device 2, with the shank portion 22 and the rear needle end portion 230 made of resilient plastic materials. The packing ring 26a may be fastened to a groove recessed in the shank portion 22 or may be integrally formed with the shank portion 22.

The needle axis 200 will be aligned with the syringe axis 100 when the needle device 2 is normally secured on a sleeve portion 12 of the syringe means 1 for injection purpose.

Each biasing socket 27 generally conical shaped includes: a conical bottom 271, a conical apex 272 tapered forwardly from the conical bottom 271, and a longitudinal conical axis 270 aligned with the conical apex 272 to be generally perpendicular to the conical bottom 271 and to be inclinedly deviated from the needle axis 200 of the needle device 2 to define an acute angle A between the needle axis 200 and the longitudinal conical axis 270 of the biasing socket 27. The conical bottom 271 includes a ratchet-tooth recess 271a circumferentially recessed in a rear portion of the shank portion 22 and tapered radially rearwardly from the conical bottom 271 of the biasing socket 27. The biasing socket 27 is snugly engageable with an arrowhead portion 301 of the plunger means 3 for obliquely biasing the needle device 2 when coupled to the plunger means 3 and retracted in the syringe cylinder 11 after finishing an injection.

The plunger means 3 includes: a thin-disk plunger 31a slidably held in the syringe cylinder 11 of the syringe means 3, a coupling member 30 integrally formed on a front portion of the plunger 31 having the arrowhead portion 301 formed on a front end of the coupling member 30 operatively insertable in the biasing socket 27 formed in the needle device 2, with the rear needle end portion 230 confined within the diverging port 122 formed in a rear portion of a sleeve portion 12 of the syringe means 1, a plunger rod 35 integrally secured with a plunger handle 37 and protruding rearwardly from the plunger 31a and integrally connected to the plunger for pushing operation of the plunger 31a with the plunger 31a to be rearwardly retained on the an annular extension 16 formed in a rear portion of the syringe cylinder 11 for restricting a rear movement of the plunger 31a, and a plunger axis 300 longitudinally defined at a central portion of the syringe means 3 normally aligned with a needle axis 200 of the needle device 2, and aligned with the syringe axis 100 of the syringe means 1.

The coupling member 30 includes: the arrowhead portion 301 being conical shaped and engageable with the biasing socket 27 of conical shape of the needle device 2 having an apex of the arrowhead portion 301 aligned with the plunger axis 300, the needle axis 200 and the syringe axis 100 as shown in FIG. 1 ready for a normal medical injection, a neck portion 302 connected between the arrowhead portion 301 and the plunger 31a.

The arrowhead portion 301 is formed with a ratchet tooth 301a circumferentially disposed around a rear end perimeter of the arrowhead portion 301 to be engaged with the ratchet-tooth recess 271a in the biasing socket 27 in the needle device 2 for ensuring a firm engagement of the coupling member 30 with the socket 27 of the needle device 2 for reliably coupling the needle device 2 with the plunger 31a when retracted into the syringe cylinder 11.

The plunger 31a is formed with an annular recess 311a along a periphery of the plunger 31a for embedding an annular packing ring 38 in the annular recess 311a for a smooth sealable sliding of the plunger 31a in the syringe cylinder 11. The annular packing ring 38 may have a cross section of circular shape, but not limited in this invention.

When using the present invention for injection use as shown in FIG. 2, the plunger 31a may be pushed forwardly to boost the medicine 4 in the cylinder 11 through the needle device 2 to a patient's body.

The arrowhead portion 301 of the coupling member 30 will then be forcibly inserted into the biasing socket 27 of the needle device 2 to squeeze, and expansively bifurcate the rear needle portion 230 of the needle device 2 to store a resilient potential energy of the bifucated rear needle portion, thereby operatively coupling the coupling member 30 with the needle device 2 as shown in FIG. 3.

After retracting, the plunger 31a and the coupled needle device 2 into the bore portion 10 of the syringe cylinder 11 as shown in FIG. 4, the biasing socket 27 of the needle device 2 will be restored to be snugly engaged with the arrowhead portion 301 of the coupling member 30 of the plunger means 3 by releasing a resilient force accumulated on the rear needle portion 230 when forcibly coupling the arrowhead portion 301 with the biasing socket 27 as shown in FIG. 3, thereby automatically obliquely biasing the needle device 2 coupled on the plunger 31a as shown in FIG. 4. After re-protruding the needle device 2 outwardly, the needle tip 211 will be retarded against a shoulder portion formed in a front portion of the cylinder 11, thereby bending the needle 2 and obstructing its outward protrusion and preventing its injury or contamination to the surroundings.

The present invention is superior to the earlier invention, U.S. Pat. No. 5,328,475, also issued to the same inventor of this application since the the thick larger plunger 31 of the earlier invention has been minimized to merely include a thin-disk plunger 31a and an annular packing ring 38 jacketed on the plunger 31a, thereby saving cost and being helpful for environmental protection.

The plunger rod 35 may include three blades 351 protruding radially from a plunger axis 300 of the plunger means 3.

The arrowhead portion 301, the neck portion 302, the plunger rod 35 and the handle 37 are all integrally formed such as made by plastic molding process, and the annular ring 38 is then embedded in the recess 311a of the thin-disk plunger 31a.

I claim:

1. A safety syringe comprising:

a syringe means including a syringe cylinder having a hollow bore portion for filling liquid medicine therein, and a sleeve portion formed on a front portion of said syringe means having a central opening formed through the sleeve portion, a syringe axis longitudinally defined in a central portion of said syringe means;

a needle device including a hollow needle portion fixed on a shank portion held in said sleeve portion of said syringe means having a biasing socket generally conical shaped recessed in a rear needle portion of said needle device including a conical bottom, a conical apex tapered forwardly from the conical bottom and a longitudinal conical axis aligned with the conical apex and obliquely deviating an acute angle from a needle axis which is longitudinally defined in a central portion of said needle device and is aligned with the syringe axis of said syringe means when the needle device is held on said syringe means for injection; and a plunger means slidably held in said syringe cylinder for boosting liquid medicine in said cylinder for injection through said needle device, and a coupling member formed on said plunger having an arrowhead portion formed at a front end of said coupling member operatively forcibly inserted in said biasing socket to couple the arrowhead portion with the needle device to store a resilient restoring energy of the rear needle portion of said needle device after finishing an injection, and upon retraction of the plunger and the needle device coupled to said plunger into said syringe cylinder, said needle device will be automatically restored and obliquely biased to prevent outwardly re-protruding of said needle device from said syringe means;

the improvement which comprises:

said plunger means including a thin-disk plunger having said arrowhead portion integrally formed at a front portion of said plunger and integrally connected to said plunger by a neck portion, and an annular packing ring embedded in an annular recess circumferentially recessed in said thin-disk plunger for slidably holding said plunger in said syringe cylinder, with said arrowhead portion formed with a ratchet tooth circumferentially disposed around a rear end portion of said arrowhead portion, and with said plunger having a plunger rod integrally secured with a plunger handle protruding rearwardly from and integrally connected with said plunger; and said biasing socket in said needle device having a ratchet-tooth recess circumferentially recessed in a rear needle portion and tapered radially rearwardly from the conical bottom of said biasing socket for a firm engagement between said ratchet tooth on said arrowhead portion of said plunger means with said ratchet-tooth recess in said needle device for stably coupling said needle device with said plunger means when finishing the injection.

* * * * *

UNITED STATES PATENT AND TRADEMARK OFFICE
CERTIFICATE OF CORRECTION

PATENT NO. : 5,405,327
DATED : 11 April 1995
INVENTOR(S) : Long-Hsiung CHEN

It is certified that error appears in the above-indentified patent and that said Letters Patent is hereby corrected as shown below:

On the title page,

[76] Inventor:   Long-Hsiung CHEN, 5F, No. 91-3, Chung Cheng Rd., Sec. 1, Taipei, Taiwan, R.O.C.

Please change the address for the inventor as shown on the patent to read as shown above.

Signed and Sealed this

Thirty-first Day of October 1995

Attest:

BRUCE LEHMAN

Attesting Officer

Commissioner of Patents and Trademarks